United States Patent [19]
Ross

[11] Patent Number: 5,974,614
[45] Date of Patent: Nov. 2, 1999

[54] TRIPLE BRUSH GUM BLASTER

[76] Inventor: Keith B. Ross, 13275 S. St. Lawrence Ave., Chicago, Ill. 60627

[21] Appl. No.: 09/032,819

[22] Filed: Mar. 2, 1998

[51] Int. Cl.[6] ............................. A46B 11/02; A61C 17/22
[52] U.S. Cl. ................................. 15/22.2; 15/24
[58] Field of Search .................... 15/22.1, 22.2, 15/24, 29; 601/141, 142

[56] References Cited

U.S. PATENT DOCUMENTS

| | | | |
|---|---|---|---|
| 1,908,509 | 5/1933 | Davis | 15/167.2 |
| 2,172,624 | 9/1939 | Romani | 15/22.1 |
| 2,214,407 | 9/1940 | Deutsch | 15/167.2 |
| 3,072,938 | 1/1963 | Phaneuf | 15/22.1 |
| 3,535,047 | 10/1970 | Vireno | 401/10 |
| 3,562,566 | 2/1971 | Kircher | 15/22.2 |
| 4,060,870 | 12/1977 | Cannarella | 15/24 |
| 4,223,417 | 9/1980 | Solow | 15/22.1 |
| 4,638,520 | 1/1987 | Eickmann | 15/22.1 |
| 4,845,795 | 7/1989 | Crawford et al. | 15/22.1 |
| 5,120,225 | 6/1992 | Amit | 15/22.1 |
| 5,142,723 | 9/1992 | Lustig et al. | 15/22.1 |
| 5,244,298 | 9/1993 | Greenhouse | 401/191 |
| 5,301,381 | 4/1994 | Klupt | 15/22.1 |
| 5,321,866 | 6/1994 | Klupt | 15/22.1 |
| 5,383,242 | 1/1995 | Bigler et al. | 15/22.1 |
| 5,407,287 | 4/1995 | Braun et al. | 401/176 |
| 5,439,014 | 8/1995 | Moussa | 132/311 |
| 5,442,827 | 8/1995 | Hommann | 15/22.1 |
| 5,504,958 | 4/1996 | Herzog | 15/22.1 |
| 5,504,959 | 4/1996 | Yukawa et al. | 15/22.2 |
| 5,528,786 | 6/1996 | Porat et al. | 15/22.1 |

*Primary Examiner*—Mark Spisich
*Assistant Examiner*—Theresa T. Snider
*Attorney, Agent, or Firm*—Davis & Kendall, PC; Tyrone Davis; John S. Kendall

[57] ABSTRACT

An improved toothbrush which allows the user to brush the teeth and gums simultaneously while using a minimal forward and backward arm stroke, and minimize the time required for dental hygiene. The invention consists of three brushes, one inner and two outer sets of bristles. The outer brushes are designed to fit over the upper and lower gum area to clean, stimulate, and massage the entire gum.

11 Claims, 4 Drawing Sheets

TRIPLE BRUSH GUM BLASTER

BACKGROUND OF THE INVENTION

1. Field of the Invention

The present invention relates to the field of cleaning devices, and more particularly relates to a new and improved automatic cleaning device having an improved electromechanical characteristics for cleaning, polishing, and scrubbing. In the preferred embodiment a toothbrush is adapted in such a way as to clean the top portion of the gum area, scrub and polish the teeth, and clean the bottom gum area simultaneously.

2. Description of the Prior Art

Currently, there are various cleaning devices available on the open market. These devices are earmarked for either cleaning, polishing or massaging the oral cavity primarily the gums. These devices have included bristles, and brushes which effect a cleaning and polishing to creases, crevices, and hard to reach areas. Many are powered devices which have bristles in the same plane which rotate to impart a cleaning action.

Such prior powered bristles, for example are disclosed in U.S. Pat. No. 4,845,795 to Crawford et al. wherein the individual bristle tufts rotate back and forth by a gearing action. In U.S. Pat. No. 5,142,723 to Lustig et al. has the bristles rotate about their axis in the same plane and further includes a reservoir for dispensing a dental spray.

Braun et al. U.S. Pat. No. 5,407,287 discloses a fountain toothbrush having a reservoir in its handle for dispensing toothpaste to the bristles. The cleaning action is imparted by the user's hand movements. Cannarella, U.S. Pat. No. 4,060,870 also discloses a device for dispensing a paste and cleaning fluids.

In a more traditional approach Davis, Deutsch, and Vireno, U.S. Pat. Nos. 1,908,509, 2,214,407, and 3,535,047 respectively disclose dental cleaning brushes having bristles in opposite planes. These devices contemplate the hand movement of the user to impart the cleaning action. Klupt, in U.S. Pat. No. 5,321,866 discloses a toothbrush having an electromechanical paste delivery system. While Greenhouse U.S. Pat. No. 5,244,298 discloses a manual paste delivery system for the toothbrush.

An alternative method of dental hygiene is the use of liquid jet devices, these devices draw fluid from a reservoir and direct fine sprays to a small dental area. These clean and provide some gum stimulation, however these devices are cumbersome, messy to use, and attack only small surfaces at a time. Additionally, they are not considered portable or suitable for travel.

It is therefore an object of this novel invention to provide a portable multi functional dental hygiene device to clean the teeth, stimulate the gums, and dispense a dental paste. Another object of this invention is to provide an electromechanical device to clean and polish teeth while simultaneously cleaning and massaging the gums.

Another object of the invention is to provide a dental hygiene tool which allows persons with arthritic limbs and disabilities to effect dental hygiene with a minimum of movement.

A further object of the invention is to provide a dental cleaning device suitable for travel and stimulate the gums.

Additional objects, advantages and novel features of the invention will be set forth in part in the description which follows, and in part will become apparent to those skilled in the art upon examination of the following or may be learned by practice of the novel invention. The objects and advantages of the method may be realized and attained by means of the instrumentalities and combinations particularly pointed out in the appended claims.

To achieve the foregoing and other objects and in accordance with the purpose of the present invention, as embodied and broadly described herein, the novel invention a device having three spaced apart heads and a toothpaste compartment in the handle, a toothpaste delivery system, and diamond shaped equi-length bristles. The outer row of bristles bend inwardly, while the inner row of bristles are straight. The bristles effectively clean the teeth and stimulate the gums.

SUMMARY OF THE INVENTION

The present invention relates to a improved toothbrush which allows the user to brush the teeth and gums simultaneously while using a minimal forward and backward arm stroke, and minimize the time required for dental hygiene. The invention consists of three brushes, one inner and two outer sets of bristles. The outer brushes are designed to fit over the upper and lower gum area to clean, stimulate, and massage the entire gum. This promotes blood circulation throughout the gum area and reduces plaque, thereby preventing the occurrence of gum disease. The middle brush incorporates a toothpaste delivery system and cleans the tooth enamel.

More specifically, the three brushes move in a horizontal direction. The two outer brushes move in cinque to clean the gums with the middle brush moving in a reverse horizontal direction cleaning the teeth enamel. The brushes snap into the stem portion of the holder and are disposable. The stem is attached to the handle. A water-resistant storage container within the base of the handle is used as storage for dental paste, liquid or toothpaste. The invention has a dual action motor which powers the brushes and acts as a pump for dispensing the toothpaste to the middle brush. A thumb switch is located along the side of the handle. The switch allows the user to turn it on and control the brushing motion either fast or slow speed. A button activates a pumping action which dispenses toothpaste to the brush.

BRIEF DESCRIPTION OF THE DRAWINGS

The accompanying drawings, which are incorporated in and form a part of the specification, illustrate the present invention and, together with the description, serve to explain the principles of the invention. In the drawings.

DETAILED DESCRIPTION OF THE INVENTION

Figure 1:
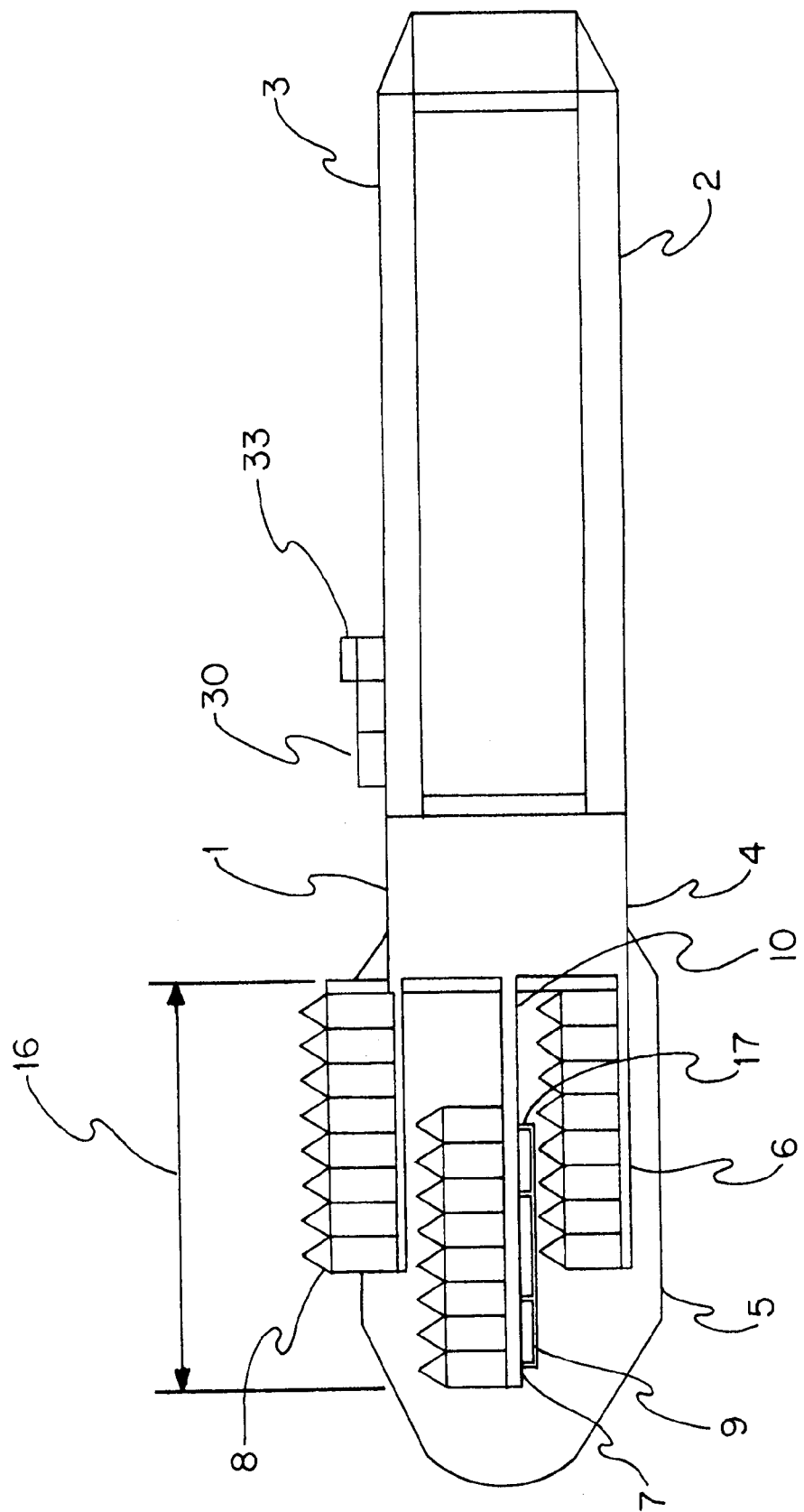
FIG. 1 shows an embodiment of the invention.
Figure 2:
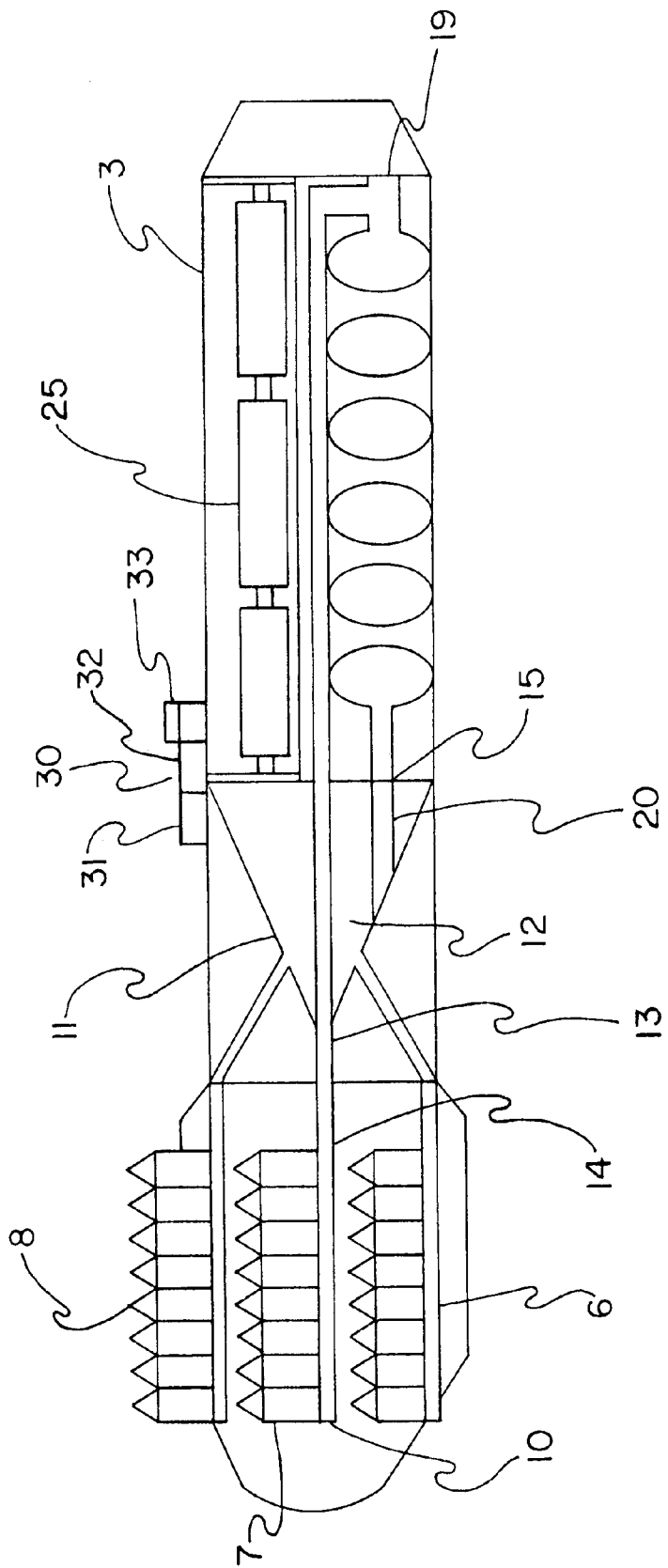
FIG. 2 is a cutaway showing the hollow cavity in the housing.

Referring to FIGS. 1 and 2, in FIG. 1 the Triple Brush Gum Blaster (1) has a housing (2) made of either durable plastic or metal. This housing (2) forms a handle (3). A connecting stem (4) attaches to the head (5). The head includes three sets of brushes (6, 7, and 8). The middle brush having an opening (9), and a hollow cavity (10) running the length of the brush (7). The brushes (6, 7, and 8) move in a horizontal direction (16). The brushes (6, 7, and 8) are activated by a motor (11). The motor (11) causes the brushes (6, 7, and 8) to move in a rapid motion along a horizontal axis. The brushes (6, 7, and 8) are offset so that the two outer brushes (6, and 8) move in cinque, with the middle brush (7) moving in an opposite direction to the outer brushes (6, and 8).

The connecting stem (4) has a cavity (12). The motor (11) is disposed in the cavity (12). In addition the stem includes a hollow capillary (13) extending its length. The capillary (13) having two ends (14, and 15). The first end (14) attached to the opening (9) in the middle brush (7). The second end (15) is attached to a dispensing cavity (18) located in the handle (3). The dispensing cavity (18) has two openings (19, and 20). The first opening (19) allows the user to insert a dental paste or creme. The second opening (20) is connected to the motor (11). A thumb switch (30) on the handle (3) has three settings, slow (31), fast (32), and a dispensing button (33). Upon depressing the dispensing button (33), the user activates the motor (11) which pushes air into the dispensing cavity (18) causing the paste to move through the capillary (13) through the hollow cavity (10) and up through the middle brush (7).

Figure 3:
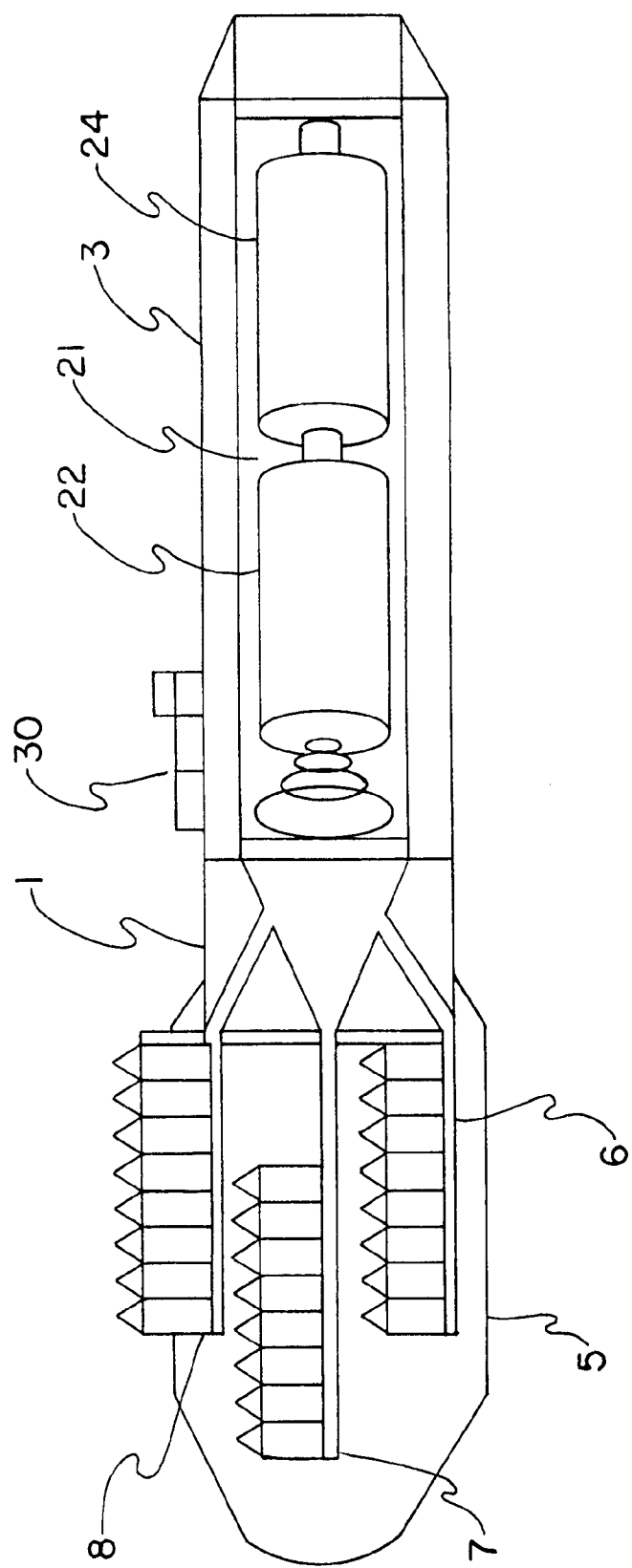
FIG. 3 shows another embodiment of the invention.
Figure 4:
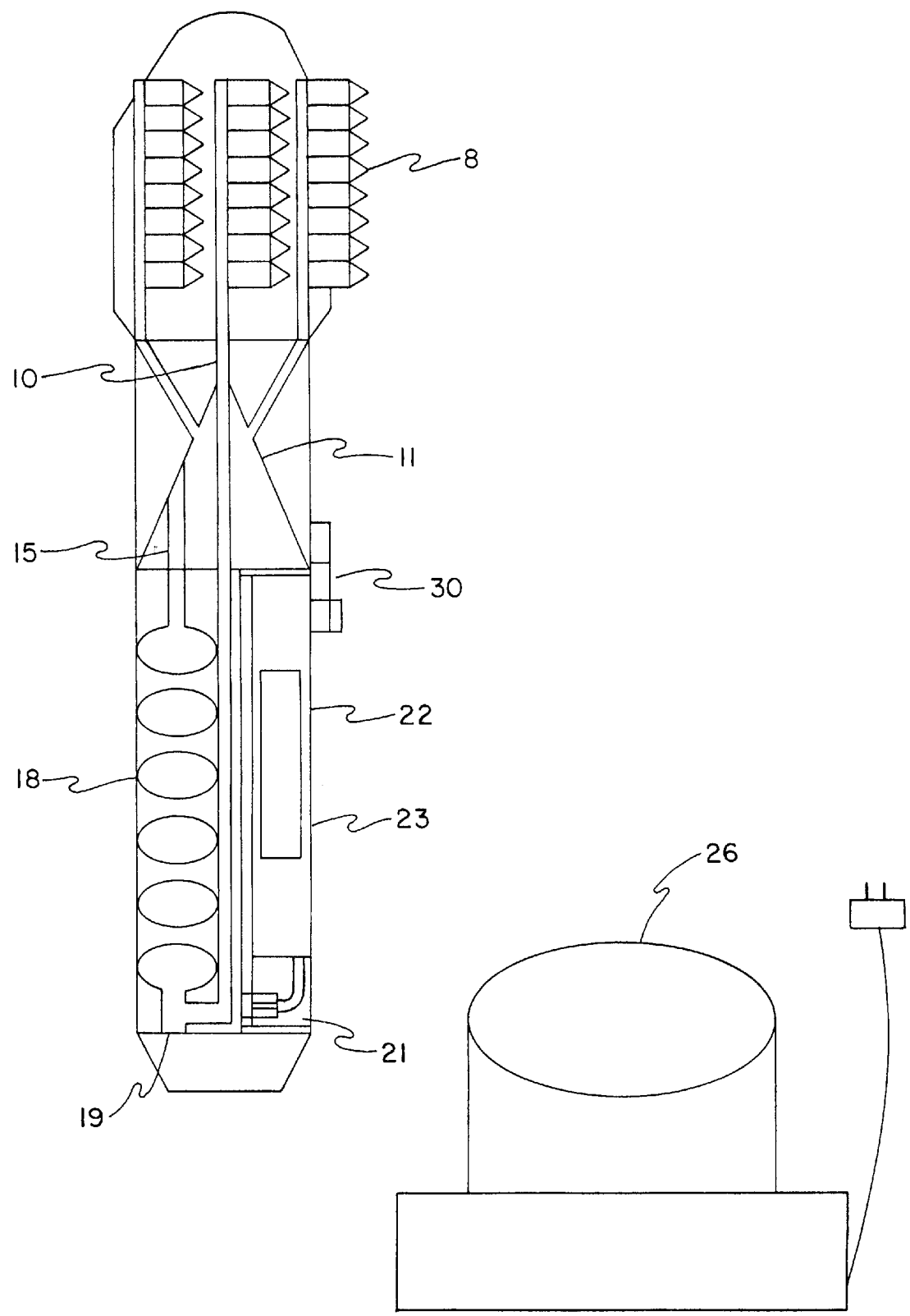
FIG. 4 shows a final embodiment of the invention.

Referring to FIGS. 3, and 4 the handle (3) has a second cavity (21). This second cavity (21) carries the power supply (22). The power supply (22) can be either C batteries (24), AAA batteries (25), or NiCad rechargable batteries (23). FIG. 4, shows an embodiment of the invention having as a power source NiCad rechargeable batteries (23). This embodiment of the invention having a separate recharging unit and stand (26).

In the preferred embodiment, the user presses the thumb switch (30) activating the dispensing button (33). The motor (11) pushes air into the dispensing cavity (18) causing the dental paste to move through the capillary (13) and into the hollow cavity (10) and out through dispensing orifices (17). After the desired amount of dental paste is dispersed on the middle brush (7), the user may chose either the fast (32) or slow (31) setting. By choosing either of the settings, the user activates the motor (11) causing the outer brushes (6, and 8) to move in a horizontal direction. The middle brush (7) also moves in a horizontal direction but is offset from the outer brushes (6, and 8). This causes the middle brush (7) to move in an opposite horizontal direction from the outer brushes (6, and 8). The outer brushes (6, and 8) massage and clean the gums. While the movement of the middle brush (7) simultaneously cleans the tooth enamel. As a result of the horizontal movement of the brushes (6, 7, and 8), the user need only position the Triple Brush Gum Blaster (1) strategically in the mouth to clean several teeth with little hand motion. Thus, eliminating the need for vigorous hand and arm motion by the user. In addition, the Triple Brush Gum Blaster (1) significantly reduces th time to complete dental hygiene activites.

When considering the above, it is understood that the novel invention can be accomplished with the apparatus disclosed, as well as, with various changes in the arrangement without departing from the scope and spirit of the invention.

The embodiments of the invention in which an exclusive property or privilege is claimed are defined as follows:

1. A dental hygiene apparatus for massaging and cleaning comprising:
    a housing having a first and a second cavity disposed therein;
    a stem connected to said housing and said stem including a hollow area, said stem having a capillary having first and second ends running the length of said stem;
    a head attached to said stem, said head having two outer brushes and an inner brush;
    means for power disposed in said hollow area of said stem having the ability to impart horizontal motion to said inner and outer brushes and pump air to said first cavity of said housing;
    said housing further comprises an elongated shape having front and rear ends and an inner and outer area, a thumb switch is attached to said outer area; and
    said first cavity comprises a storage chamber containing a dental cleaner and said second cavity comprises a storage chamber for batteries.

2. The dental hygiene apparatus as recited in claim 1, wherein said inner brush further comprises several dispensing orifices along its length and being connected to a hollow cavity throughout, said hollow cavity having an opening, and said opening being attached to said first end of said capillary.

3. The dental hygiene apparatus as recited in claim 2 wherein said second end of said capillary is attached to said first cavity allowing said dental cleaner passage therefrom.

4. The dental hygiene apparatus as recited in claim 3 wherein said inner and outer brushes move in a rapid horizontal direction and said inner brush offset from said outer brushes thereby causing said inner brush to move in an opposite direction from said outer brushes.

5. The dental hygiene apparatus as recited in claim 4 wherein said dental cleaner is from the group consisting of a liquid or a paste.

6. The dental hygiene apparatus as recited in claim 5 wherein said means for power is a dual action motor.

7. The dental hygiene apparatus as recited in claim 6 wherein said thumb switch operates three settings.

8. A dental hygiene apparatus for massaging and cleaning comprising:
    a housing having a cavity disposed therein;
    a stem connected to said housing and said stem including a hollow area, said stem having a capillary having first and second ends running the length of said stem;
    a head attached to said stem, said head having two outer brushes and an inner brush;
    means for power disposed in said hollow area of said stem having the ability to impart a rapid motion in a horizontal direction to said inner and outer brushes; and
    said housing further comprising an elongated shape having front and rear ends and an inner and outer area, a thumb switch is attached to said outer area, and whereby said cavity comprises a storage chamber for batteries.

9. The dental hygiene apparatus as recited in claim 8 wherein said thumb switch operates two settings.

10. The dental hygiene apparatus as recited in claim 9 wherein said inner and outer brushes move in a rapid horizontal direction and said inner brush being offset from said outer brushes thereby causing said inner brush to move in an opposite direction from said outer brushes.

11. The dental hygiene apparatus as recited in claim 10 wherein said means for power is a two staged motor.

* * * * *